US009974930B2

(12) United States Patent
Lupton et al.

(10) Patent No.: US 9,974,930 B2
(45) Date of Patent: *May 22, 2018

(54) GUIDE WIRE FOR USE IN RE-CANALISING A VASCULAR OCCLUSION IN A HUMAN OR ANIMAL SUBJECT

(71) Applicant: Brivant Research & Development Limited, Galway (IE)

(72) Inventors: Henry William Lupton, Oranmore (IE); Mark Bruzzi, Galway (IE)

(73) Assignee: Brivant Research & Development Limited, Galway (IE)

( * ) Notice: Subject to any disclaimer, the term of this patent is extended or adjusted under 35 U.S.C. 154(b) by 3 days.

This patent is subject to a terminal disclaimer.

(21) Appl. No.: 15/220,741

(22) Filed: Jul. 27, 2016

(65) Prior Publication Data
US 2016/0331943 A1  Nov. 17, 2016

Related U.S. Application Data

(63) Continuation-in-part of application No. 13/337,490, filed on Dec. 27, 2011, now Pat. No. 9,802,026.
(Continued)

(51) Int. Cl.
*A61M 25/00* (2006.01)
*A61M 25/09* (2006.01)
*A61B 17/22* (2006.01)

(52) U.S. Cl.
CPC ............ *A61M 25/09* (2013.01); *A61B 17/22* (2013.01); *A61B 2017/22042* (2013.01); *A61M 2025/09083* (2013.01); *A61M 2025/09175* (2013.01)

(58) Field of Classification Search
CPC ........ A61M 25/09; A61M 2025/09175; A61M 2025/09083
(Continued)

(56) References Cited

U.S. PATENT DOCUMENTS 2,349,336 A  *  5/1944  Batchelder ........... B26D 1/0006
                                          225/103
3,674,014 A      7/1972  Tillander
(Continued)

FOREIGN PATENT DOCUMENTS

FR         1465723       3/1967
JP       1994505646      6/1994
(Continued)

OTHER PUBLICATIONS

Canadian Office Action, Application No. 2,557,726, dated May 13, 2011.
(Continued)

*Primary Examiner* — Adam J Eiseman
*Assistant Examiner* — Jonathan M Foreman
(74) *Attorney, Agent, or Firm* — Michael F. Scalise

(57) ABSTRACT

A guidewire (1) for re-canalizing a vascular occlusion comprises a core wire (5) which terminates at its distal end (4) in a terminal member (7) for opening the occlusion. A helical coil sleeve (10) extends around the core wire (5) from the terminal member (7) to a location (11) along the core wire (5). The terminal member (7) defines first and second planar surface portions (13, 14), which converge towards a distal transversely extending leading edge portion (8). In use, as the terminal member (7) is urged through the vascular occlusion, the first and second surface portions (13, 14) act on the occlusion to form an opening therethrough. A distal portion (28) of the core wire (5) is of spade-like configuration for facilitating bending thereof for directing the terminal member (7) out of a central major plane (35) defined by the distal portion (28) for facilitating aligning of the terminal member (7) with a branched vessel of the vascular system.

16 Claims, 12 Drawing Sheets

Related U.S. Application Data which is a continuation of application No. 10/590,866, filed as application No. PCT/IE2005/000031 on Mar. 24, 2005, now Pat. No. 8,092,395.

(58) Field of Classification Search
USPC .............. 600/433, 434, 585; 606/159, 170; 604/164.13
See application file for complete search history.

(56) References Cited

U.S. PATENT DOCUMENTS

| | | | |
|---|---|---|---|
| 3,850,158 A | 11/1974 | Elias et al. | |
| 5,116,350 A | 5/1992 | Stevens | |
| 5,127,917 A | 7/1992 | Niederhauser et al. | |
| 5,135,483 A | 8/1992 | Wagner et al. | |
| 5,303,714 A | 4/1994 | Abele et al. | |
| 5,365,942 A | 11/1994 | Shank | |
| 5,423,846 A | 6/1995 | Fischell | |
| 5,527,298 A | 6/1996 | Vance et al. | |
| 5,876,356 A * | 3/1999 | Viera | A61L 31/022 600/585 |
| 6,132,389 A | 10/2000 | Cornish et al. | |
| 6,235,007 B1 | 5/2001 | Homet et al. | |
| 6,348,040 B1 | 2/2002 | Stalker et al. | |
| 6,491,648 B1 | 12/2002 | Cornish et al. | |
| 6,522,909 B1 | 2/2003 | Garibaldi et al. | |
| 6,669,652 B2 | 12/2003 | Anderson et al. | |
| 8,092,395 B2 | 1/2012 | Lupton et al. | |
| 2002/0019644 A1 | 2/2002 | Hastings et al. | |
| 2003/0013993 A1 | 1/2003 | Jafari et al. | |
| 2005/0004585 A1 | 1/2005 | Hall et al. | |
| 2005/0065453 A1 | 3/2005 | Shabaz et al. | |
| 2006/0184186 A1 | 8/2006 | Noone et al. | |

FOREIGN PATENT DOCUMENTS

| | | |
|---|---|---|
| JP | 199843304 | 2/1998 |
| JP | 199933120 | 2/1999 |
| JP | 2002514474 | 5/2002 |
| JP | 2005144104 | 6/2005 |
| WO | 9208510 | 5/1992 |
| WO | 9842399 | 10/1998 |

OTHER PUBLICATIONS

Japanese Decision for Refusal dated Mar. 8, 2011, Patent Application 2007-504558, English Translation.

Japanese Office Action dated Mar. 8, 2011, Patent Application No. 2007-504558.

Japanese Notification of Reasons for Refusal dated Jul. 13, 2010, Patent Application 2007-504558, English Translation.

* cited by examiner

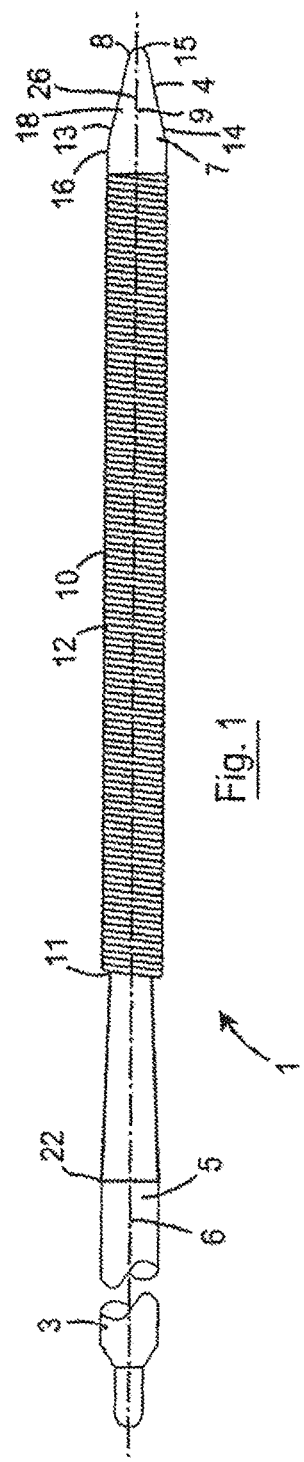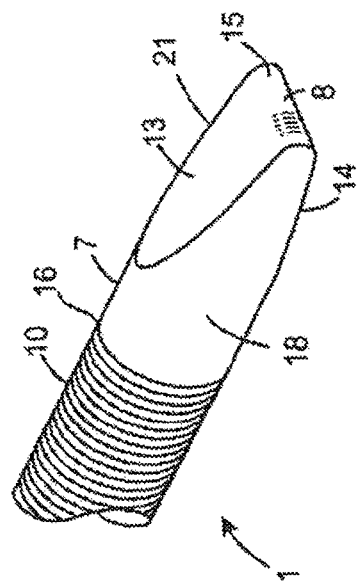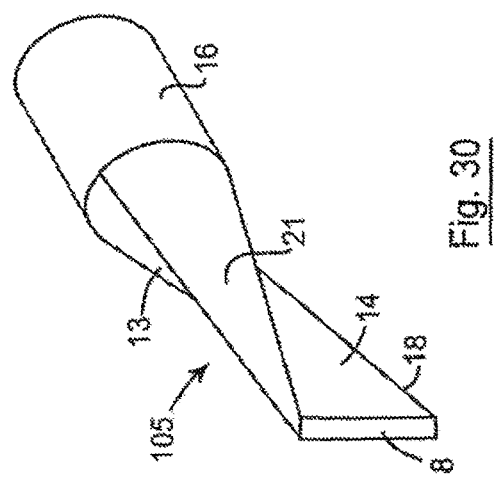

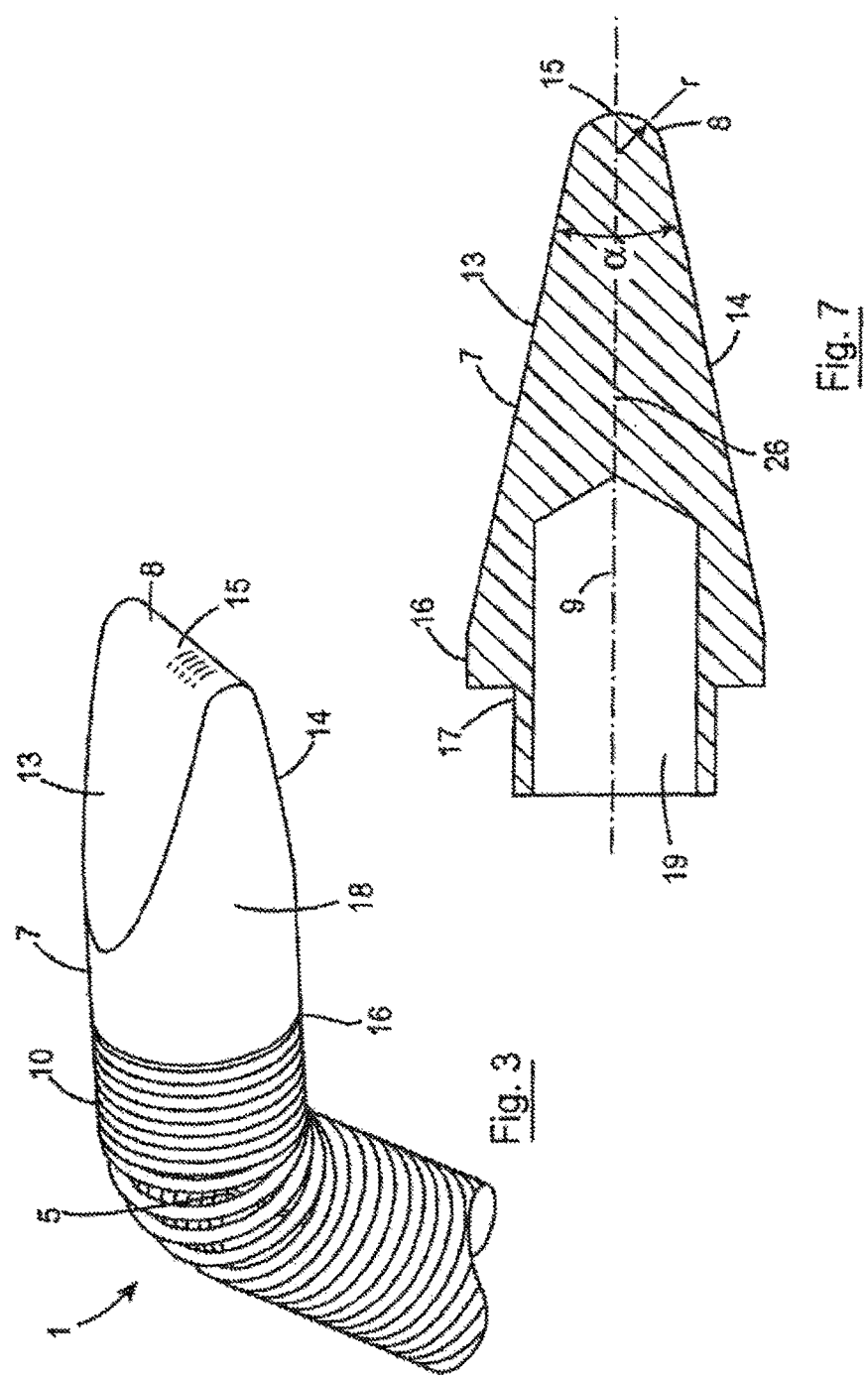

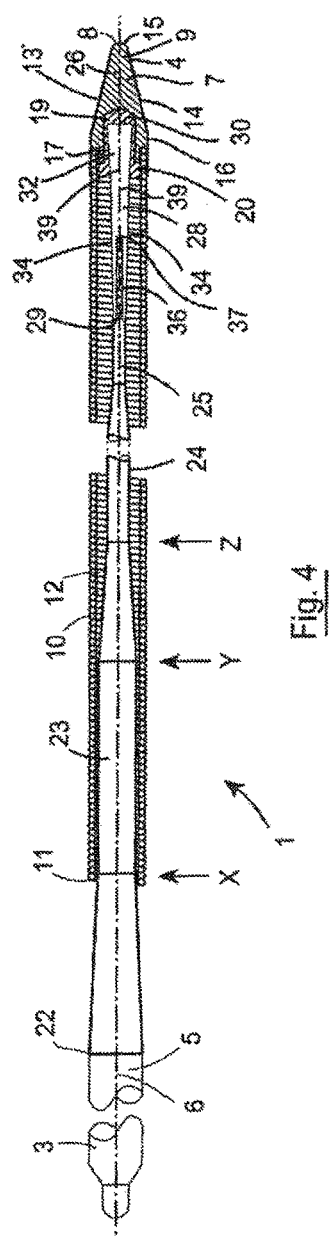
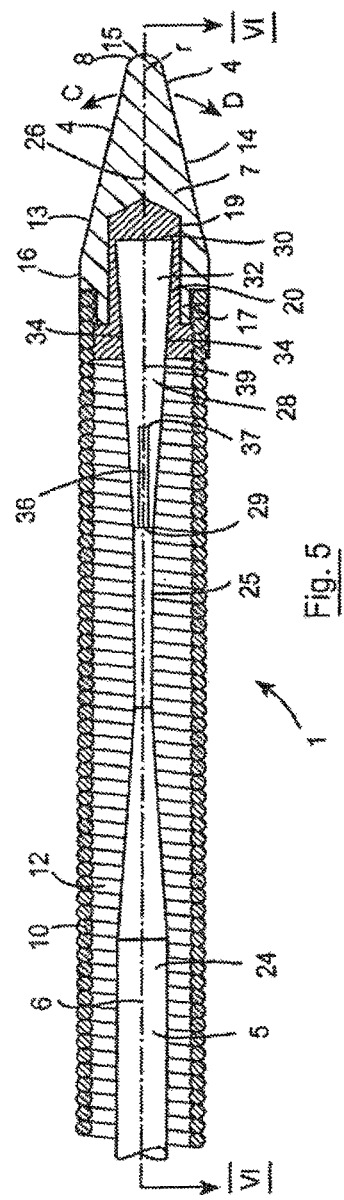

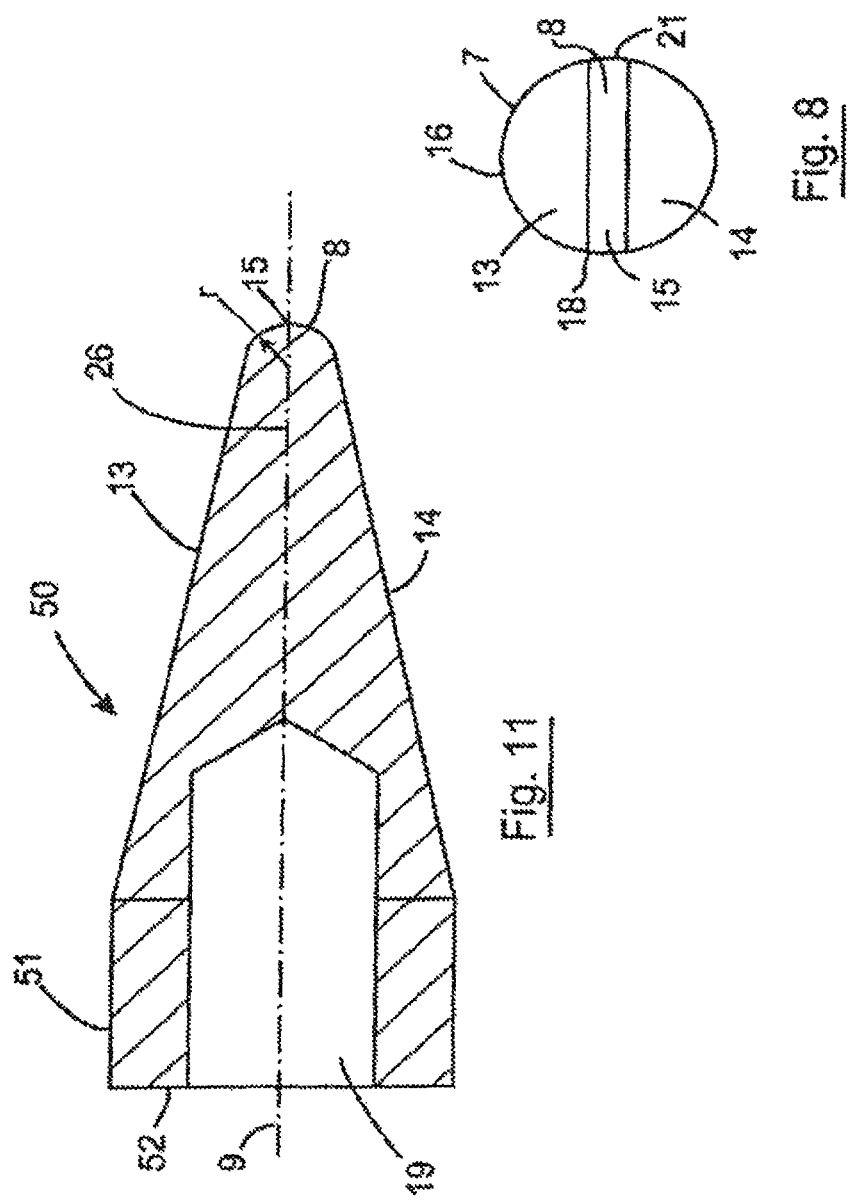

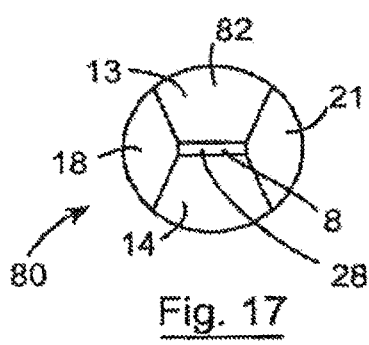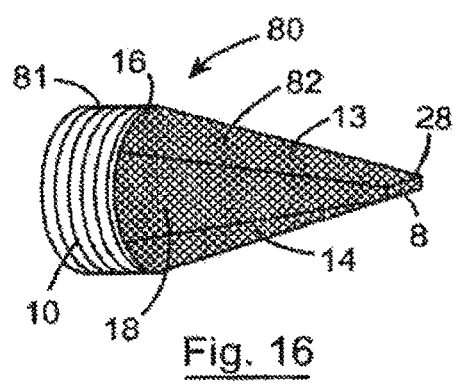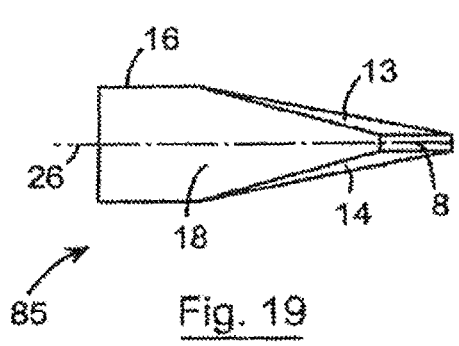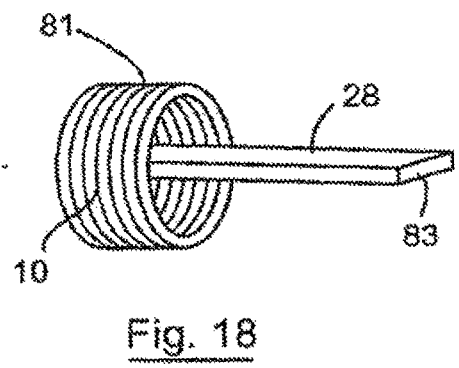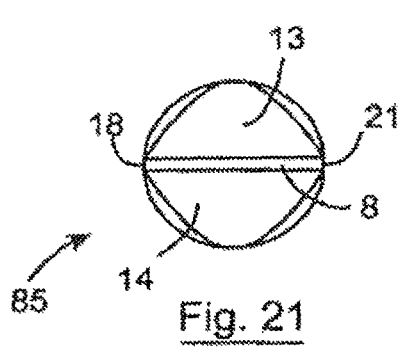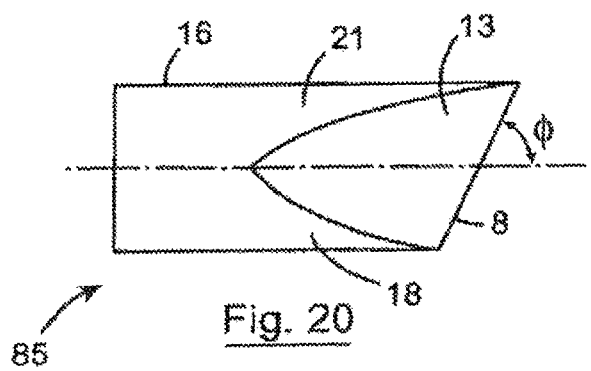

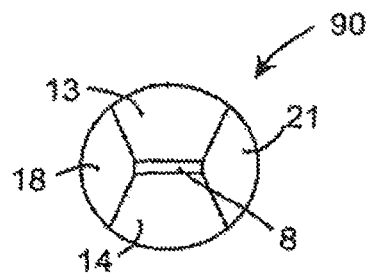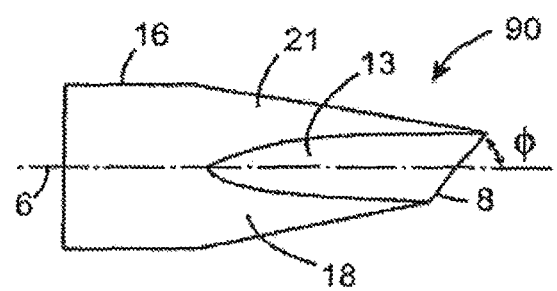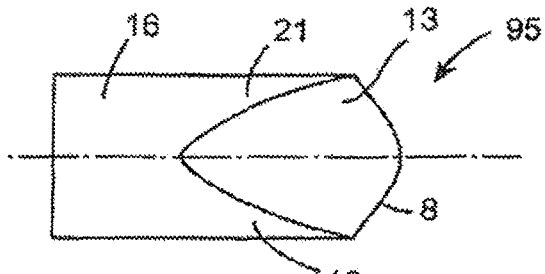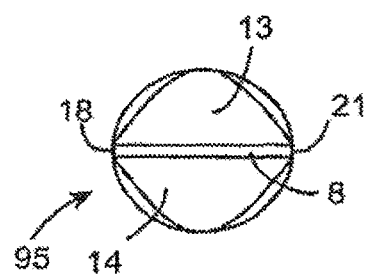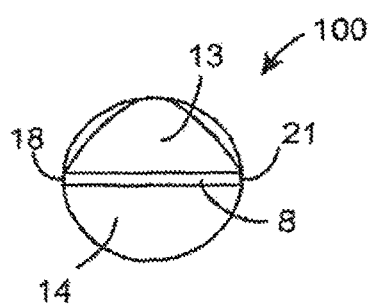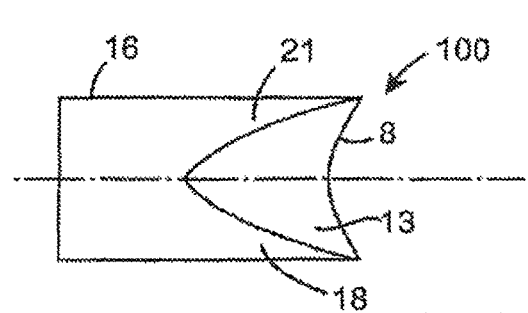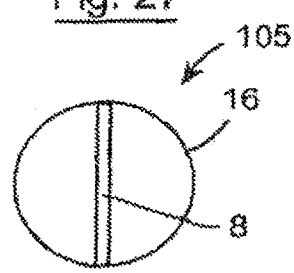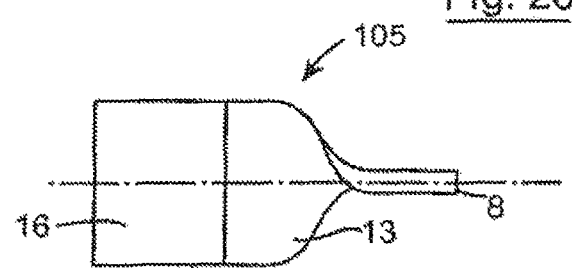

GUIDE WIRE FOR USE IN RE-CANALISING A VASCULAR OCCLUSION IN A HUMAN OR ANIMAL SUBJECT

CROSS-REFERENCE TO RELATED APPLICATIONS

This application is a continuation-in-part of U.S. patent application Ser. No. 13/337,490, filed on Dec. 27, 2011, which is a continuation of U.S. patent application Ser. No. 10/590,866, filed on Sep. 19, 2006, now U.S. Pat. No. 8,092,395, which is a National Stage Entry of International application No. PCT/IE05/00031, filed on Mar. 25, 2005.

BACKGROUND OF THE INVENTION

The present invention relates to a guide wire for use in a re-canalising process of a vascular occlusion in a human or animal subject, and in particular, for re-canalising a blocked or partially blocked artery, for example, in the cardiovascular system, although the invention is not limited to a guide wire for such use. The invention also relates to a method for re-canalising a vascular occlusion in a human or animal subject.

Guide wires are commonly used for guiding a catheter carrying a therapeutic or other device to a remote location in the vascular system of a subject. For example, where a vessel is occluded or partially occluded, a guide wire is used for guiding a catheter which may carry a balloon or a stent at its distal tip for locating in the artery in the occluded part thereof for maintaining a passage through the occlusion. However, prior to the insertion of the stent or other such device, the occlusion must be penetrated in order to open a passage therethrough for accommodating the stent.

Guide wires are provided for penetrating such occlusions or partial occlusions prior to the insertion of the catheter over the guide wire. U.S. Pat. No. 6,348,040 of Stalker, et al discloses such a catheter which is provided with a vibrating tip. However, a disadvantage of the guide wire disclosed in this U.S. patent specification is that in order to provide the vibrating tip, relatively expensive and, more importantly, cumbersome equipment is required, which must be attached to the guide wire U.S. Pat. No. 6,669,652 of Anderson, et al discloses a guide wire, which comprises a core wire and a helical coil extending around a distal portion of the core wire. The helical coil extends beyond the distal end of the core wire, and tapers to a distal point for penetrating the occlusion as the guide wire is urged forwardly. One disadvantage of the guide wire disclosed in this U.S. specification is that due to the fact that the tip is pointed, there is a danger of the tip penetrating the wall of a vessel of the vascular system as the guide wire is being urged to the occlusion. Another disadvantage of this guide wire is that the portion of the helical coil which extends beyond the distal end of the core wire is relatively flaccid, and thus renders the guide wire difficult to guide through the vascular system, and in particular a vascular system with branched vessels.

U.S. Pat. Nos. 5,527,298 and 5,127,917 disclose guide wires in which the distal end of the guide wires terminate in bulbous distal tip portions. The distal tip portions are of transverse cross-sectional area significantly greater than the transverse cross-sectional area of the guide wire, and taper to a distal point. The distal point facilitates penetration of the occlusion, and the tapering portion facilitates in easing the guide wire through the occlusion. However, a disadvantage of the guide wires disclosed in these two U.S. patent specifications is that due to the fact that the transverse cross-sectional area of the bulbous distal tip portions are significantly greater than the transverse cross-sectional area of the guide wire, difficulty is experienced in subsequently urging a catheter over the bulbous tip portions.

There is therefore a need for a guide wire which is suitable for use in a re-canalising process of a vascular occlusion in a human or animal subject.

SUMMARY OF THE INVENTION

The present invention is directed towards providing such a guide wire, and the invention is also directed towards providing a method for re-canalising a vascular occlusion in a human or animal subject.

According to the invention there is provided a guide wire for use in a re-canalising process for re-canalising a vascular occlusion in a human or animal subject, the guide wire extending between a proximal end and a distal end, and defining a longitudinally extending main central axis, wherein the guide wire terminates at its distal end in a terminal member extending axially from the guide wire, the terminal member tapering to a distal leading tip portion for engaging and gradually opening the occlusion as the terminal member is urged therethrough.

Preferably, the leading edge portion is an elongated leading edge portion. Advantageously, the leading edge portion extends in a direction at an angle relative to an axial direction defined by the main central axis.

In one embodiment of the invention the leading edge portion extends in a direction at an angle in the range of 1° to 90°. relative to an axial direction defined by the main central axis. Preferably, the leading edge portion extends in a direction at an angle in the range of 45° to 90° relative to an axial direction defined by the main central axis. Advantageously, the leading edge portion extends in a direction at an angle of approximately 60° relative to an axial direction defined by the main central axis.

In one embodiment of the invention the leading edge portion extends in a direction substantially transversely of the main central axis.

In one embodiment of the invention a first surface portion of the terminal member converges towards an opposite second surface portion thereof towards the leading edge portion.

In another embodiment of the invention the first surface portion of the terminal member is planar.

In a further embodiment of the invention the first surface portion of the terminal member is convex in a longitudinal direction relative to the main central axis.

In a still further embodiment of the invention the first surface portion of the terminal member is concave in a longitudinal direction relative to the main central axis.

In a still further embodiment of the invention the first surface portion of the terminal member is sequentially convex and concave in a longitudinal direction relative to the main central axis.

In one embodiment of the invention a distal portion of the first surface portion of the terminal member is concave in a longitudinal direction relative to the main central axis.

In another embodiment of the invention a proximal portion of the first surface portion of the terminal member is convex in a longitudinal direction relative to the main central axis.

In another embodiment of the invention the first surface portion of the terminal member is convex in a transverse direction relative to the main central axis.

In a further embodiment of the invention the second surface portion of the terminal member converges towards the first surface portion towards the leading edge portion.

In one embodiment of the invention the second surface portion of the terminal member is planar.

In another embodiment of the invention the second surface portion of the terminal member is convex in a longitudinal direction relative to the main central axis.

In a further embodiment of the invention the second surface portion of the terminal member is concave in a longitudinal direction relative to the main central axis.

In a still further embodiment of the invention the second surface portion of the terminal member is sequentially convex and concave in a longitudinal direction relative to the main central axis.

In a still further embodiment of the invention a distal portion of the second surface portion of the terminal member is concave.

In a further embodiment of the invention a proximal portion of the second surface portion of the terminal member is convex.

In one embodiment of the invention the second surface portion of the terminal member is convex in a transverse direction relative to the main central axis.

Preferably, the first and second surface portions terminate in the leading edge portion to define the leading edge portion as a chisel edge.

In one embodiment of the invention the first and second surface portions of the terminal member define an included angle in the range of 1° to 179°. Preferably, the first and second surface portions of the terminal member define an included angle in the range of 5° to 90°. Advantageously, the first and second surface portions of the terminal member define an included angle of approximately 15°.

In one embodiment of the invention the first and second surface portions of the terminal member are joined by spaced apart opposite third and fourth surface portions. Preferably, the leading edge portion of the terminal member extends between the third and fourth surface portions.

In one embodiment of the invention the third and fourth surface portions of the terminal member are planar surfaces. In an alternative embodiment of the invention the third and fourth surface portions of the terminal member are convex in a transverse direction relative to the main central axis.

In another embodiment of the invention the third and fourth surface portions of the terminal member are parallel to each other in an axial direction defined by the main central axis.

Alternatively, the third and fourth surface portions of the terminal member taper towards the leading edge portion.

In one embodiment of the invention the third and fourth surface portions of the terminal member define an included angle in the range of 1° to 179°. Preferably, the third and fourth surface portions of the terminal member define an included angle in the range of 5° to 90°. Advantageously, the third and fourth surface portions of the terminal member define an included angle of approximately 15°.

In one embodiment of the invention the third surface portion of the terminal member is convex in a longitudinal direction relative to the main central axis. Alternatively, the third surface portion of the terminal member is concave in a longitudinal direction relative to the main central axis.

In another embodiment of the invention the third surface portion of the terminal member is sequentially convex and concave in a longitudinal direction relative to the main central axis.

In a still further embodiment of the invention a distal portion of the third surface portion of the terminal member is concave in a longitudinal direction relative to the main central axis, and in a further embodiment of the invention a proximal portion of the third surface portion of the terminal member is convex in a longitudinal direction relative to the main central axis.

In one embodiment of the invention the fourth surface portion of the terminal member is convex in a longitudinal direction relative to the main central axis. Alternatively, the fourth surface portion of the terminal member is concave in a longitudinal direction relative to the main central axis.

In one embodiment of the invention the fourth surface portion of the terminal member is sequentially convex and concave in a longitudinal direction relative to the main central axis. In a further embodiment of the invention a distal portion of the fourth surface portion of the terminal member is concave in a longitudinal direction relative to the main central axis, and in a still further embodiment of the invention a proximal portion of the fourth surface portion of the terminal member is convex in a longitudinal direction relative to the main central axis.

Preferably, the leading edge portion is radiused from the first surface portion of the terminal member to the second surface portion thereof. Advantageously, the leading edge portion is radiused in plan view.

In another embodiment of the invention the leading edge portion is convex in plan view. Alternatively, the leading edge portion is concave in plan view.

In one embodiment of the invention the maximum outer transverse cross-sectional area of the terminal member is substantially similar to the outer transverse cross-sectional area of the guide wire adjacent the terminal member. Preferably, the outer transverse cross-sectional area of the terminal member adjacent the guide wire is similar to the outer transverse cross-sectional area of the guide wire adjacent the terminal member so that the outer surface of the terminal member is in axial alignment with the outer surface of the guide wire adjacent the terminal member. Advantageously, the guide wire adjacent the terminal member and the terminal member adjacent the guide wire are of circular transverse cross-section, and are of substantially similar outer diameters.

Advantageously, the transverse width of the leading edge portion is substantially similar to the transverse width of the guide wire adjacent the terminal member in a plane containing the leading edge portion and extending parallel to the main central axis.

In one embodiment of the invention the guide wire comprises an elongated core wire extending from the proximal end to the distal end. Preferably, the terminal member is secured to the distal end of the core wire.

Advantageously, the core wire terminates in a distal portion of rectangular transverse cross-section defining first and second opposite major surfaces joined by first and second opposite minor surfaces for facilitating bending thereof for offsetting the terminal member relative to the main central axis for facilitating guiding of the terminal member into a branched vessel of a vascular system.

In one embodiment of the invention the first and second major surfaces of the distal portion of the core wire converge towards each other towards the distal end thereof. Alternatively, the first and, second major surfaces of the distal portion of the core wire extend substantially parallel to each other.

In another embodiment of the invention the first and second minor surfaces of the distal portion of the core wire diverge from each other towards the distal end thereof. Alternatively, the first and second minor surfaces of the distal portion of the core wire extend substantially parallel to each other.

In one embodiment of the invention a reinforcing means is provided on the distal portion of the core wire for minimising axial twisting thereof.

In another embodiment of the invention the first and second major surfaces of the distal portion of the core wire define therebetween a central major plane extending parallel to the main central axis and cutting the first and second minor surfaces, and the distal portion is curved in the central major plane for offsetting the terminal member relative to the main central axis for in turn facilitating guiding of the terminal member into a branched vessel of a vascular system.

Preferably, the central major plane defined by the first and second major surfaces of the distal portion of the core wire extends transversely of a plane containing the leading edge portion of the terminal member and extending parallel to the main central axis.

Advantageously; the central major plane defined by the first and second major surfaces of the distal portion of the core wire extends substantially parallel to a plane containing the leading edge portion of the terminal member and extending parallel to the main central axis.

In one embodiment of the invention the core wire extending from the distal portion thereof to the proximal end is of circular transverse cross-section.

In another embodiment of the invention a sleeve extends along the core wire from the terminal member and terminates at a location intermediate the distal end and the proximal end of the core wire. Preferably, the sleeve is of external circular transverse cross-section. Advantageously, the external diameter of the sleeve is substantially similar to the diameter of the terminal member adjacent the guide wire. Ideally, the sleeve comprises a helical coil located around the core wire adjacent the distal end thereof.

In one embodiment of the invention a plug extends from the terminal member adjacent a proximal end thereof for engaging an internal bore defined by the sleeve for securing the sleeve to the terminal member.

Preferably, the terminal member is secured to the sleeve by brazing or soldering.

Advantageously, a core wire engaging bore extends into the terminal member for engaging the distal end of the core wire.

Preferably, the core wire engaging bore extends axially into the terminal member.

Advantageously, the terminal member is secured to the core wire by brazing, soldering, welding or adhesive. Ideally, the soldering or brazing, soldering, welding or adhesive material is a radiopaque material.

In one embodiment of the invention the terminal member is of radiopaque material.

In another embodiment of the invention at least a portion of the terminal member is of a magnetic material for facilitating urging of the terminal member through a vascular system by a magnetic urging means located externally of the subject.

In a further embodiment of the invention the terminal member is of a magnetic material.

In one embodiment of the invention a distal portion of the guide wire is of a magnetic material for facilitating urging of the terminal member through a vascular system by a magnetic urging means located externally of the subject.

The invention also provides in combination the guide wire according to the invention and a magnetic urging means for urging the terminal member through a vascular occlusion.

Preferably, the magnetic urging means for urging the terminal member through a vascular system to a vascular occlusion.

The invention also provides a method for re-canalising a vascular occlusion in a human or animal subject, the method comprising urging the terminal member of the guide wire according to the invention through the occlusion for gradually opening thereof.

Preferably, the terminal member is urged by the guide wire through a vascular system to the occlusion prior to being urged through the occlusion.

Advantageously, the terminal member is urged through the occlusion by a magnetic urging means located externally of the subject.

Ideally, the terminal member is urged through a vascular system by a magnetic urging means located externally of the subject.

The advantages of the invention are many. The guide wire according to the invention is particularly suitable for use in re-canalising a vascular occlusion in a vascular system in a human or animal body, and in particular, for use re-canalising an occluded or partially occluded vessel in the cardiovascular system of the human or animal body. By virtue of the fact that the terminal member tapers to a distal leading edge portion, the distal leading edge portion initially engages the vascular occlusion, and as the terminal member is urged through the vascular occlusion, the tapering portion of the terminal member gradually opens the occlusion, until the terminal member opens the occlusion to define a bore of transverse cross-section corresponding to the maximum external transverse cross-sectional area of the terminal member.

By providing the terminal member to be of transverse cross-sectional area substantially similar to that of the guide wire, so that the outer surface of the terminal member is aligned with and substantially coincides with the outer surface of the guide wire, a catheter can be readily easily passed over the guide wire and over the terminal member, without snagging on the terminal member.

A particular advantage is achieved when the terminal member terminates in a transversely extending distal leading edge portion. The transversely extending leading edge portion facilitates ease of penetration of the vascular occlusion, and subsequent gradual opening of the vascular occlusion as the transversely extending leading edge portion is urged through the occlusion. By providing the terminal member with respective opposite first and second surface portions which converge towards each other towards the distal leading tip portion, a particularly advantageous form of the terminal member is obtained, and the terminal member is particularly suitable for gradually opening the vascular occlusion as the terminal member is urged therethrough. By providing the first and second converging surface portions as planar surface portions, a further advantage is achieved in that the rate of penetration of the occlusion can be maintained relatively constant through the constant increase in surface contact. Tapering the third and fourth surface portions of the terminal member further enhances this advantage.

The provision of the terminal member with a first surface portion which is either convex or concave, or is sequentially convex and concave from the proximal to the distal end thereof, provides a gradual transition from the tapering portion of the terminal member to the guide wire.

By providing the terminal member of a magnetic material, the terminal member can be urged through the vascular system by a magnetic field generated by a suitable magnetic urging device located externally of the subject. This has the added advantage that the terminal member can be urged through the vascular system by the magnetic field, rather than by pushing the guide wire into the subject. By being able to urge the terminal member through the vascular system by an externally generated magnetic field in particular facilitates in directing the terminal member into a branched vessel of a vascular system, without the need to pre-bend the guide wire. Additionally, by urging the terminal member by an externally generated magnetic field, the risk of puncturing a vessel of the vascular system as the terminal member is being urged therethrough is minimized.

Additionally, since it is important that the guide wire remain flexible in order to negotiate the tortuous vascular systems of the anatomy, by magnetically pulling the guide wire through the vascular system, the guide wire can be provided to be considerably more flexible than would be the case where the guide wire is being provided to be pushed through the vascular system. The more flexible a guide wire is, the less easy it is to guide it through the vascular system by pushing. Thus, in order to facilitate relatively accurate guiding of a guide wire through the vascular system which is to be pushed through the vascular system, the guide wire must be of lesser flexibility than where the guide wire is being pulled through the vascular system. Additionally, by providing the guide wire to be magnetically pulled through the vascular system, there is a lesser risk of the terminal member entering a false lumen between the laminae of a vessel.

BRIEF DESCRIPTION OF THE DRAWINGS

The invention will be more clearly understood from the following description of some preferred embodiments thereof, which are given by way of example only, with reference to the accompanying drawings, in which:

FIG. 1 is a side elevational view of a guide wire according to the invention, FIG. 2 is a perspective view of a portion of the guide wire of FIG. 1, FIG. 3 is another perspective view of the portion of FIG. 2 of the guide wire of FIG. 1, FIG. 4 is a transverse cross-sectional side elevational view of the guide wire of FIG. 1, FIG. 5 is a partly transverse cross-sectional side elevational view of a portion of the guide wire of FIG. 1, FIG. 7 is a transverse cross-sectional side elevational view of a portion of the guide wire of FIG. 1, FIG. 8 is an end elevational view of the portion of FIG. 7 of the guide wire of FIG. 1, FIG. 11 is a transverse cross-sectional side elevational view similar to FIG. 7 of a detail similar to that of FIG. 7 of a guide wire according to another embodiment of the invention, FIG. 16 is a perspective view of a portion of a guide wire according to a further embodiment of the invention, FIG. 17 is an end elevational view of the portion of the guide wire of FIG. 16, FIG. 18 is a perspective view of a part of the portion of the guide wire of FIG. 16, FIG. 19 is a side elevational view of a portion of a guide wire according to a still further embodiment of the invention, FIG. 20 is a top plan view of the portion of the guide wire of FIG. 19, FIG. 21 is an end view of the portion of the guide wire of FIG. 19, FIG. 22 is a top plan view of a portion of a guide wire according to another embodiment of the invention, FIG. 23 is an end elevational view of the portion of the guide wire of FIG. 22, FIG. 24 is a top plan view of a portion of a guide wire according to a further embodiment of the invention, FIG. 25 is an end elevational view of the portion of the guide wire of FIG. 24, FIG. 26 a top plan view of a portion of a guide wire according to another embodiment of the invention, FIG. 27 is an end elevational view of the portion of the guide wire of FIG. 26, FIG. 28 is a top plan view of a portion of a guide wire according to another embodiment of the invention, FIG. 29 is an end elevational view of the portion of the guide wire of FIG. 28, FIG. 30 is a perspective view of the portion of the guide wire of FIG. 28.

DETAILED DESCRIPTION OF THE INVENTION

Figure 6:
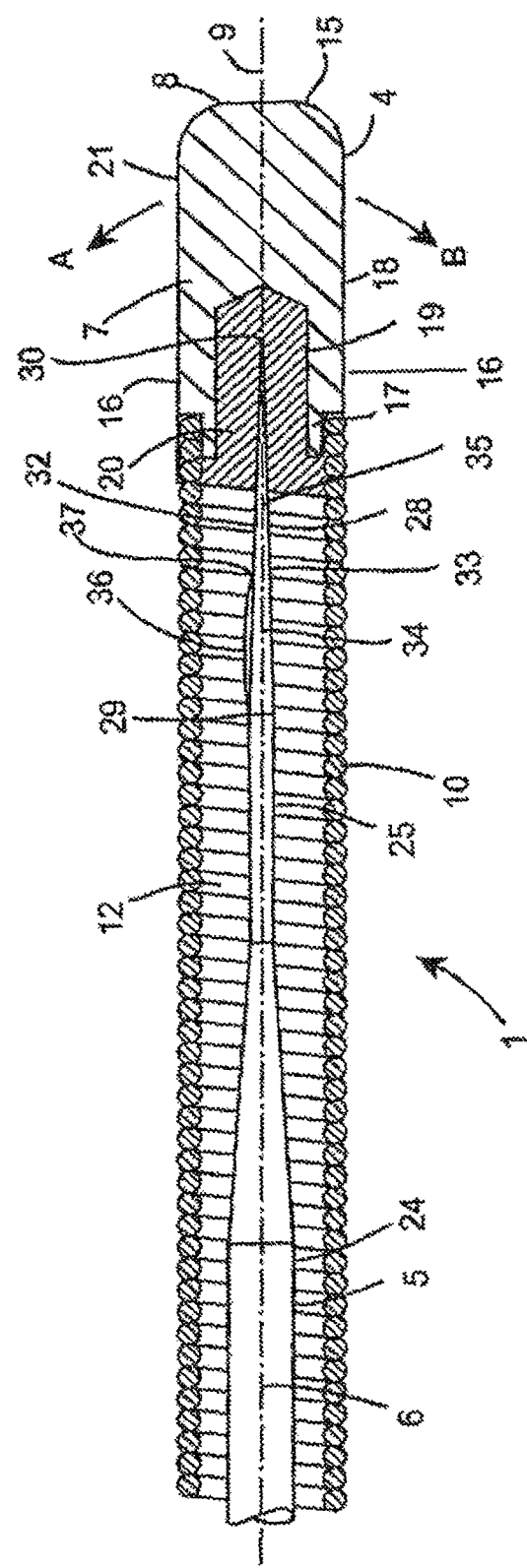
FIG. 6 is a partly transverse cross-sectional plan view of the portion of FIG. 5, on the line VI-VI of FIG. 5 of the guide wire of FIG. 1.
Figure 9:
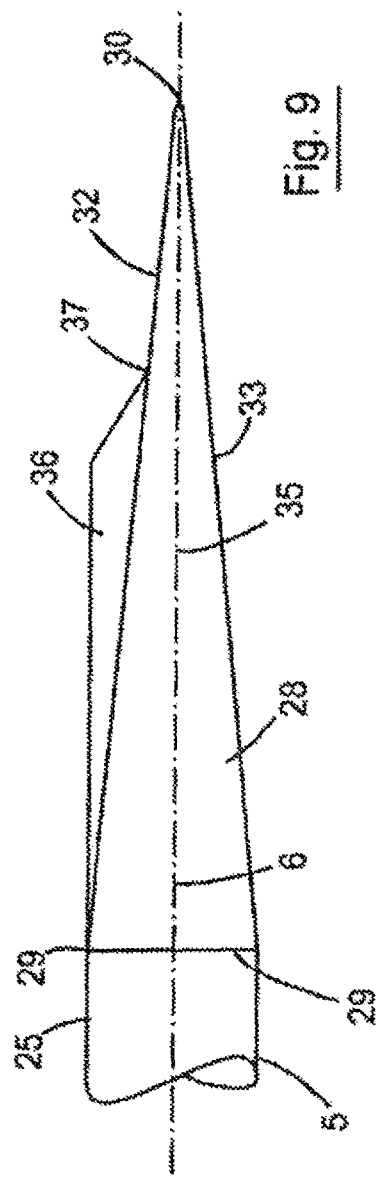
FIG. 9 is a side elevational view of another portion of the guide wire of FIG. 1.

Referring to the drawings and initially to FIGS. 1 to 10, there is illustrated a guide wire according to the invention, indicated generally by the reference numeral 1, for use in a re-canalising process for re-canalising a vascular occlusion in a vascular system of a human or animal subject. The guide wire 1 extends between a proximal end 3 and a distal end 4 and comprises a core wire 5 of circular transverse cross-section and of stainless steel material which extends from the proximal end 3 to the distal end 4, and defines a longitudinally extending main central axis 6. A terminal member 7 of circular transverse cross-section adjacent its proximal end portion 16 defines a central axis 9, and is secured to the core wire 5 at its distal end 4, and extends axially therefrom with the central axis 9 of the terminal member 7 coinciding with the main central axis 6 of the core wire 5. The terminal member 7 tapers to a distal leading edge portion, which in this embodiment of the invention is a transversely extending elongated leading edge portion 8 in the form of a chisel edge for engaging and penetrating the occlusion or partial occlusion in a vessel of the vascular system as the guide wire 1 is urged through the vascular system. The leading edge portion 8 extends at 90.degree. to the main central axis 6. A sleeve, in this embodiment of the invention provided by a tightly wound helical coil 10 of stainless steel material is secured to the terminal member 7 at the proximal end portion 16 thereof, and extends therefrom over the core wire 5, and terminates at a location 11 intermediate the proximal end 3 and the distal end 4 of the guide wire 1, but towards the distal end 4. The helical coil 10 is of circular transverse cross-section, and defines a bore 12 of circular transverse cross-section.

The terminal member 7 is of radiopaque material, in this embodiment of the invention platinum alloy, so that it is visible under X-rays as the guide wire 1 is being urged through the vascular system. The outer diameter of the terminal member 7 at its proximal end portion 16 is constant and is substantially similar to the outer diameter of the helical coil 10 adjacent the terminal member 7 so that as a catheter is being urged along the guide wire 1, the catheter can readily easily be urged over the terminal member 7. The terminal member 7 defines a first surface portion 13 and a second surface portion 14 which converge towards each other and terminate in the leading edge portion 8. In this embodiment of the invention the first and second surface portions 13 and 14 are planar, and the leading edge portion 8 is radiused, with a radius r, between the first and second surface portions 13 and 14 to form the leading edge portion 8 to be convex in a plane perpendicular to a plane containing the leading edge portion 8. The radius r of the convex surface 15 of the leading edge portion 8 is sufficiently large to provide the leading edge portion 8 to be sufficiently blunt to prevent the leading edge portion 8 penetrating a wall of a vessel of the vascular system, but not so blunt as would prevent the leading edge portion 8 penetrating an occlusion or a partial occlusion in a vessel of the vascular system. The first and second surface portions 13 and 14 define an included angle $\alpha$, see FIG. 7, which is sufficiently acute for gradually opening the occlusion as the terminal member 7 is urged therethrough, while at the same time avoiding detaching any of the occluding material from the vessel, in order to avoid urging the occluding material forwardly with the guide wire 1. The first and second surface portions 13 and 14 are joined by third and fourth surface portions 18 and 21, respectively, which extend from the proximal end portion 16 of the terminal member 7 to the leading edge portion 8. The third and fourth surface portions 18 and 21 are radiused, and are of the same radius as the outer surface of the proximal end portion 16, and thus, coincide with the outer surface of the proximal end portion 16, and are convex in a transverse direction relative to the main central axis 6.

The first and second surface portions 13 and 14 define a central major plane 26 which bisects the included angle $\alpha$ defined by the first and second surface portions 13 and 14. In this embodiment of the invention the central major plane 26 defined by the first and second surface portions 13 and 14 contains the main central axis 6 and they leading edge portion 8. The transverse width of the leading edge portion 8 is thus similar to the diameter of the proximal end portion 16 of the terminal member 7, and furthermore, the transverse cross-section of the portion of the terminal member formed by the first and second surface portions 13 and 14 is such as not to extend beyond the outer transverse cross-sectional profile of the circular proximal end portion 16 of the terminal member 7.

In this embodiment of the invention the included angle $\alpha$ defined by the first and second surface portions 13 and 14 of the terminal member 7 is approximately 15.degree., however, it is envisaged that the included angle $\alpha$ defined by the first and second surface portions 13 and 14 may be any acute angle in the range 5° to 60°, although it is believed that it is preferable that the acute angle $\alpha$ defined by the first and second surface portions 13 and 14 should lie in the range 12° to 30°. In this embodiment of the invention the radius r of the radiused convex surface 15 of the leading edge portion of the terminal member 7 is approximately 0.075 mm, although it is envisaged that the radius of the radiused convex surface 15 may lie in the range 0.02 mm, to 0.14 mm, although it is believed that it is preferable that the radius r should lie within the range 0.05 mm to 0.10 mm.

A plug 17 extends axially from the terminal member 7 for engaging the bore 12 in the helical coil 10 at the distal end thereof. The diameter of the plug 17 is such that the difference between the diameter of the plug 17 and the diameter at the proximal end portion 16 of the terminal member 7 is equal to twice the diameter of the wire forming the helical coil 10, so that when the plug member 17 is engaged in the bore 12 of the helical coil 10, the outer surface defined by the helical coil 10 substantially coincides with the outer surface of the proximal end portion 16 of the terminal member 7. A bore 19 extends axially into the plug 17 and into the terminal member 7 for accommodating the distal end 4 of the core wire 5 for securing the terminal member 7 to the core wire 5. In this embodiment of the invention the core wire 5 and the helical coil 10 are soldered to the terminal member 7 by solder 20 which fills the bore 19 as well as a distal portion of the bore 12 of the helical coil 10 for securing the terminal member 7 to the core wire 5 and the helical coil 10.

The core wire 5 commences to taper at a location 22 at the proximal side of the location 11 at which the helical coil 10 terminates, and tapers to its distal end 4. In this embodiment of the invention the core wire 5 tapers in steps as is illustrated in FIG. 4. The core wire 5 tapers from the location 22 to a first portion 23 of constant diameter, and tapers from the first portion 23 to a second portion 24 of constant diameter, and in turn tapers from the second portion 24 to a third portion 25 of constant diameter. A distal portion 28 extends from the third portion 25 at 29 to a transversely extending distal tip 30, and is of spade-like configuration having a rectangular transverse cross-section. The distal portion 28 defines a first major surface 32 and a second major surface 33, which are joined by opposite minor surfaces 34. The first and second major surfaces 32 and 33 converge towards each other towards the distal tip 30, while the minor surfaces 34 diverge away from each other towards the distal tip 30. The first and second major surfaces 32 and 33 define therebetween a central major plane 35 which contains the transversely extending distal tip 30 and the main central axis 6, and extends perpendicular to the minor surfaces 34. The spade-like configuration of the distal portion 28 facilitates bending of the guide wire at the distal portion 28 for urging the terminal member 7 out of the central major plane 35 for facilitating aligning the guide wire 1 with a branching vessel of the vascular system and directing the terminal member 7, and in turn the guide wire 1 into the branching vessel.

A reinforcing means, in this embodiment of the invention provided by a reinforcing rib 36 extends longitudinally along the first major surface 32 of the distal portion 28 from the location 29, and terminates at a location 37 intermediate the location 29 and the distal tip 30 for minimizing torsional twisting of the core wire along the distal portion 28. Where the distal portion 28 is to be bent for bending the terminal member 7 out of the central major plane 35, the distal portion 28 is bent between the location 37 and the terminal member 7.

Figure 10:
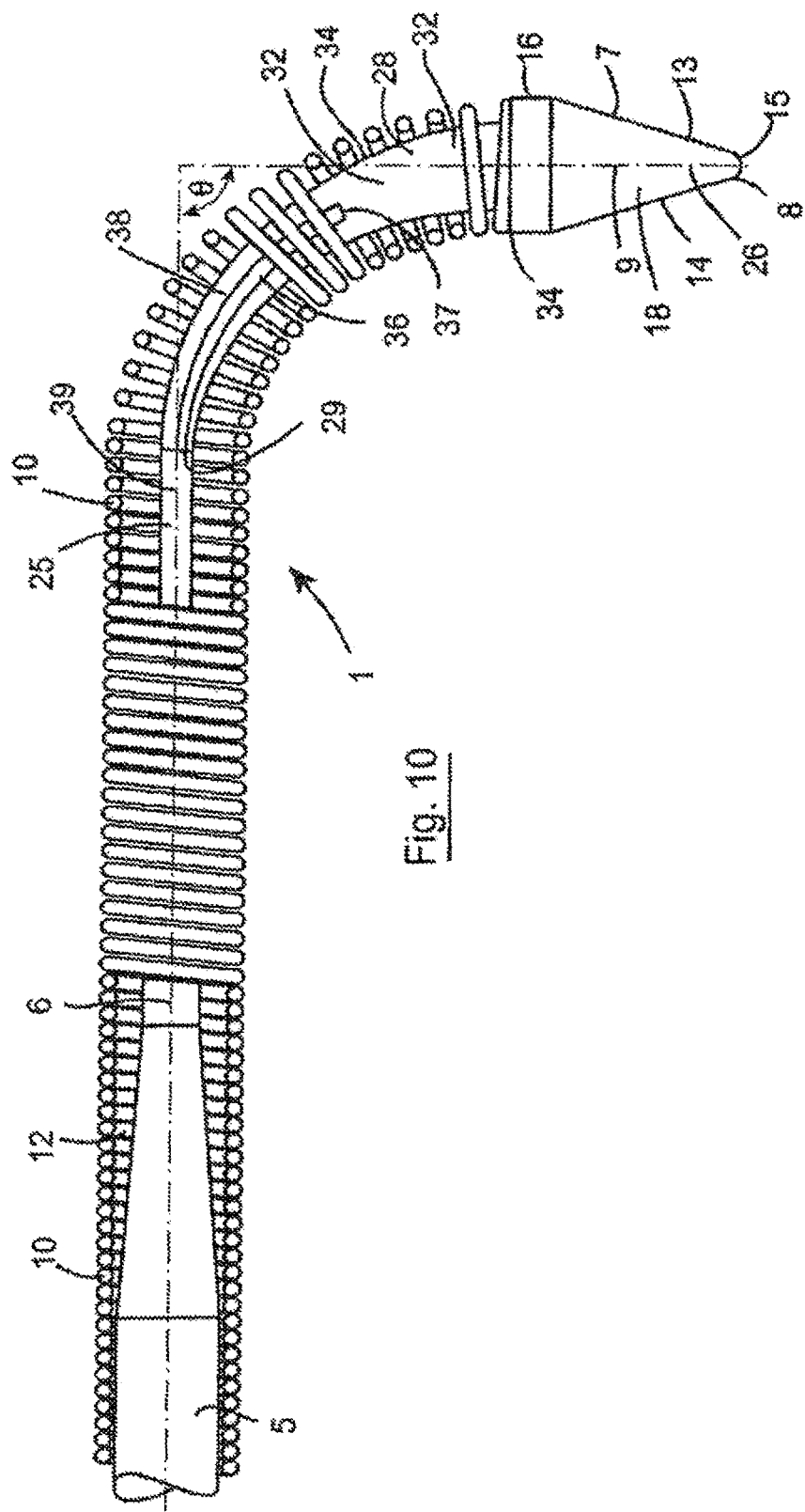
FIG. 10 is a transverse cross-sectional side elevational view of a portion of the guide wire of FIG. 1 with a portion of the guide wire curved.

A portion 38 of the distal portion 28 of the core wire 5 may be curved in the central major plane 35 as illustrated in FIG. 10 for directing the terminal member 7 out of a central minor plane 39 defined between the minor surfaces 34 and containing the main central axis 6 and extending perpendicularly of the first and second major surfaces 32 and 33. Forming the curved portion 38 in the distal portion 28 also facilitates aligning of the terminal member 7 with a branched vessel of the vascular system, and directing the terminal member 7; and in turn, the guide wire 1 into the branched vessel. When the guide wire 1 is provided with the distal portion 28 curved at 38, the distal portion 28 could still be bent between the location 37 and the terminal member 7 for directing the terminal member 7 out of the central major plane 35. In this way, the terminal member 7 would be directed out of both the major and minor central planes 35 and 39, respectively.

In practice, bending of the distal portion 28 between the location 37 and the terminal member 7 for urging the terminal member 7 out of the central major plane 35 would typically be carried out manually by a surgeon or a paramedic prior to inserting the guide wire 1 into the subject. The curved portion 38 for directing the terminal member 7 out of the central minor plane 39 would normally be factory formed.

The amount by which the curved portion 38 of the distal portion 28 is curved determines the amount by which the terminal member 7 is offset from the central major plane 35, in other words, the amount of curvature in the curved portion 38 determines the included angle θ which the central axis 9 of the terminal member 7 makes with the main central axis 6, namely, the angular offset of the terminal member 7 relative to the main central axis 6. In FIG. 10 the angle θ is illustrated as being 90°, however, it will be readily apparent to those skilled in the art that the angle θ may be any desired angle, and typically will lie between 0° and 90°. The angle at which the portion of the distal portion 28 between the location 37 and the terminal member 7 may be bent may be any desired angle, and typically would be in the range from 0° to 90°.

In this embodiment of the invention the terminal member 7 is secured to the distal portion 28 of the core wire 5 with the central major plane 26 defined by the first and second surface portions 13 and 14 extending perpendicularly to the central major plane 35 defined by the first and second major surfaces 32 and 33 of the distal portion 28 of the core wire 5. Accordingly, the leading edge portion 8 extends perpendicularly to the central major plane 35 defined by the first and second major surfaces 32 and 33 of the distal portion 28 of the core wire 5. This facilitates bending of the flattened distal portion 28 in the direction of the arrows A and B, see FIG. 6. However, it is envisaged that the terminal member 7 may be secured to the core wire 5 with the central major plane 26 defined between the first and second surface portions 13 and 14 of the terminal member 7 extending parallel to or coinciding with the central major plane 35 defined between the first and second major surfaces 32 and 33 of the distal portion 28 of the core wire 5. In which case the leading edge portion 8 would extend parallel to or coincide with the central major plane 35 defined by the first and second major surfaces 32 and 33 of the distal portion 28 of the core wire 5.

In use, the guide wire 1 is urged through the vascular system of the subject towards the occluded vessel. On reaching the occluded vessel, the guide wire is gradually urged forward and the leading edge portion 8 of the terminal member 7 engages the occlusion and commences penetration thereof. As the leading edge portion 8 penetrates the occlusion, the first and second surface portions 13 and 14 commence to gradually open the occlusion, and further urging of the guide wire 1 causes the terminal member 7 to open the occlusion with the diameter of the opening formed in the occlusion corresponding to the diameter of the terminal member 7 adjacent the guide wire 1. Further urging of the guide wire 1 through the occlusion maintains the occlusion open with a diameter corresponding to that of the terminal member 7. Thereafter a catheter (not shown) is passed over the guide wire 1 and is guided into the occlusion. If the guide wire 1 is carrying a balloon, stent or other therapeutic device, the device is located in the opening formed in the occlusion by the terminal member 7, and the guide wire 1 and the catheter (not shown) are removed.

Prior to entering the guide wire 1 into the vascular system of the subject, the guide wire 1 may be bent adjacent the terminal member 7 thereof by bending the distal portion 28 between the location 37 and the terminal member 7 in the direction of the arrows A or B for facilitating aligning of the terminal member 7 with a branched vessel of the vascular system as the guide wire 1 is being urged through the vascular system. Additionally, as mentioned above, the guide wire 1 may be supplied with the curved portion 38 already formed in the distal portion 28 as illustrated in FIG. 10, and if desired, the distal portion 28 may be bent between the location 37 and the terminal member 7 for urging the terminal member 7 out of the central major plane 35 for further enhancing alignment of the guide wire 1 with a branched vessel of the vascular system.

It is also envisaged that the terminal member 7 may be provided with wells or holes on its outer surface, in particular, along the first and second surface portions 13 and 14 for retaining therapeutic drugs or other compositions, liquid or otherwise, for assisting in urging of the guide wire 1 through the vascular system, and in particular, for assisting in urging the terminal member 7 through the occlusion or partial occlusion. Such drugs or other compositions, which may be in liquid, powder or other suitable form, may be drugs which would facilitate in dilation of a vessel, or dissolving the material of the occlusion. For example, if the occlusion were caused by a thrombosis, one of the drugs may be suitable for dissolving the thrombosis.

Referring now to FIG. 11, a terminal member, indicated generally by the reference numeral 50, of a guide wire (not shown) also according to the invention is illustrated. In this embodiment of the invention the core wire and sleeve of the guide wire are similar to the core wire 5 and the sleeve 10 of the guide wire 1 of FIGS. 1 to 10. The terminal member 50 is substantially similar to the terminal member 7, and similar components are identified by the same reference numerals. In this embodiment of the invention a proximal portion 51 of the terminal member 50 is of outer circular transverse cross-section, and the terminal member 50 terminates in a leading edge portion 8 similar to the leading edge portion 8 of the terminal member 7. However, while an axial bore 19 extends into the terminal member 50 for engaging the distal end 4 of the core wire 5, the terminal member 50 is provided without a plug similar to the plug 17 of the terminal member 7. In this case the helical coil 10 would be abutted against an end face 52, and would be brazed or soldered to the end face 52 with the outer surface defined by the helical coil coinciding with the outer surface defined by the proximal portion 51 of the terminal member 50. The soldering or brazing of the helical coil 10 to the end face 52 of the terminal member 50 could be carried out simultaneously with soldering or brazing the core wire 5 into the bore 19 of the terminal member 50, or after the terminal member 50 had been brazed or soldered to the core wire 5.

Figure 12:
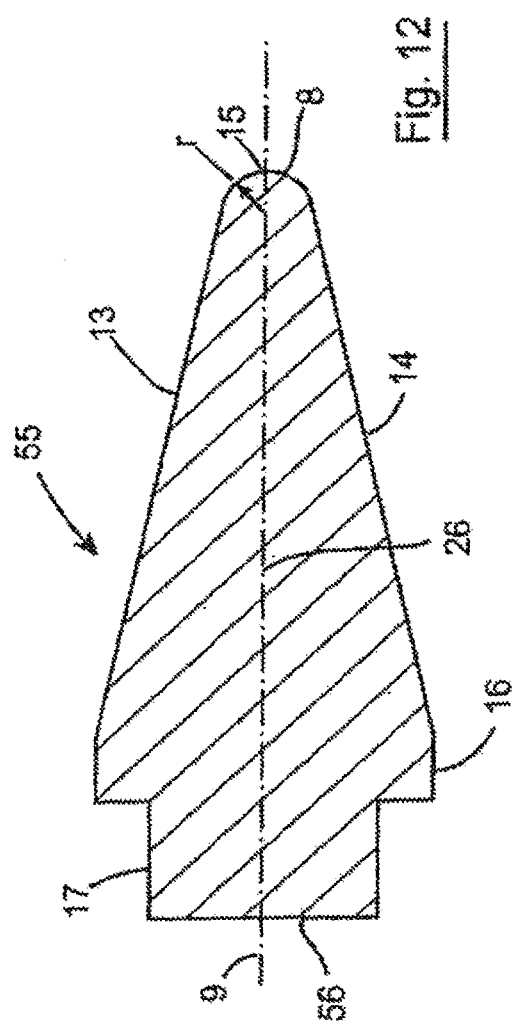
FIG. 12 is a transverse cross-sectional side elevational view similar to FIG. 7 of a detail similar to that of FIG. 7 of a guide wire according to another embodiment of the invention.

Referring now to FIG. 12, there is illustrated a terminal member 55 of a guide wire (not shown) also according to the invention. In this embodiment of the invention the core wire and the sleeve of the guide wire are similar to the core wire 5 and the sleeve 10 of the guide wire 1 of FIGS. 1 to 10. The terminal member 55 is substantially similar to the terminal member 7 and similar components are identified by the same reference numerals. In this embodiment of the invention an axial plug 17 extends from the terminal member 55, however, the terminal member 55 is provided without an axial bore similar to the axial bore 19 of the terminal member 7. Thus, in this embodiment of the invention the axial plug 17 engages the bore 12, helical coil 10, and the distal end of the core wire 5 is abutted against an end face 56 of the terminal member 55 and brazed or soldered thereto.

Figure 13:
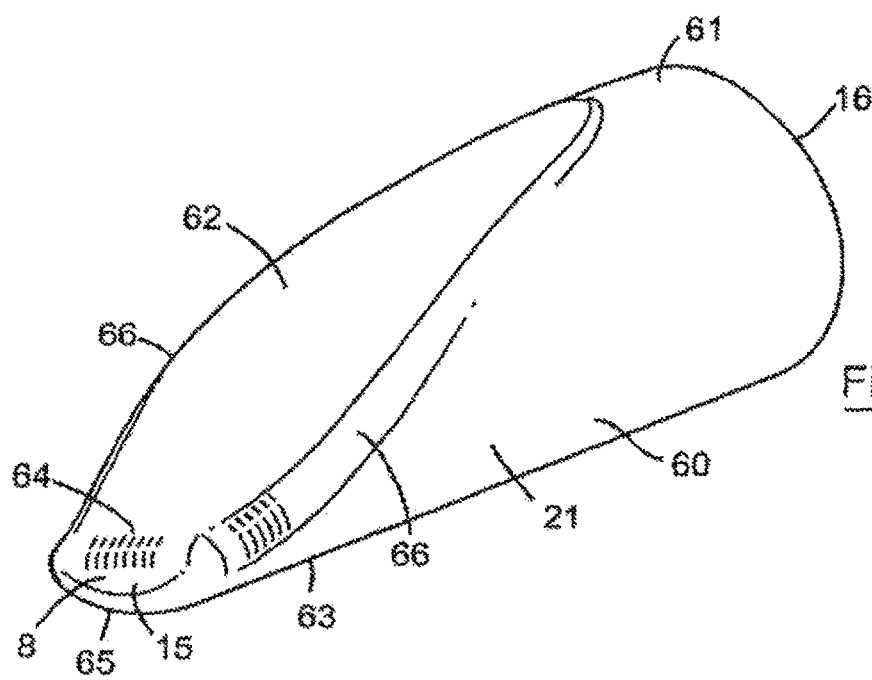
FIG. 13 is a perspective view of a portion of a guide wire according to another embodiment of the invention.

Referring now to FIG. 13, there is illustrated a terminal member 60 of a guide wire (not shown) also according to the invention. In this embodiment of the invention the core wire and the sleeve of the guide wire are similar to the core wire 5 and the sleeve 10 of the guide wire 1 of FIGS. 1 to 10. The terminal member 60 is substantially similar to the terminal member 7, and similar components are identified by the same reference numerals. The terminal member 60 comprises a proximal end portion 61 of circular transverse cross-section. However, in this embodiment of the invention the terminal member 60 comprises a first surface portion 62 which converges towards a second surface portion 63, the outer transverse cross-sectional profile of which coincides with the corresponding cross-sectional profile of the proximal end portion 61. The first surface portion 62 is convex in the longitudinal direction of the central axis 9 of the terminal member 60 and converges towards the second surface portion 63 in a direction towards the leading edge portion 8 to form with the second surface portion 63, the transversely extending leading edge portion 8. The surface 15 of the leading edge portion 8 is radiused between the first and second surface portions 62 and 63, and defines one straight edge 64 adjacent the first surface portion 62 and one arcuate edge 65 adjacent the second surface portion 63. Additionally, side edges 66 of the first surface portion 62 are radiused to merge into the outer surface of the terminal member 60. In this embodiment of the invention the straight edge 64 of the leading edge portion 8 is contained in a plane which extends parallel to a plane containing the main central axis 6, but is offset therefrom.

Otherwise, the terminal member 60 is substantially similar to the terminal member 1.

The advantage of the terminal member 60 is that since the straight edge 64 of the leading edge portion 8 is offset from the main central axis 6, the guide wire according to this embodiment of the invention can be guided through a vascular system to access a space between layers of a vessel. This, thus, permits angioplasty or other surgical procedures to be carried out in a new sub-intimal lumen. Sub-intimal angioplasty is a technique where a lumen is created between the layers of the vessel adjacent to the true lumen of the vessel.

Figure 14:
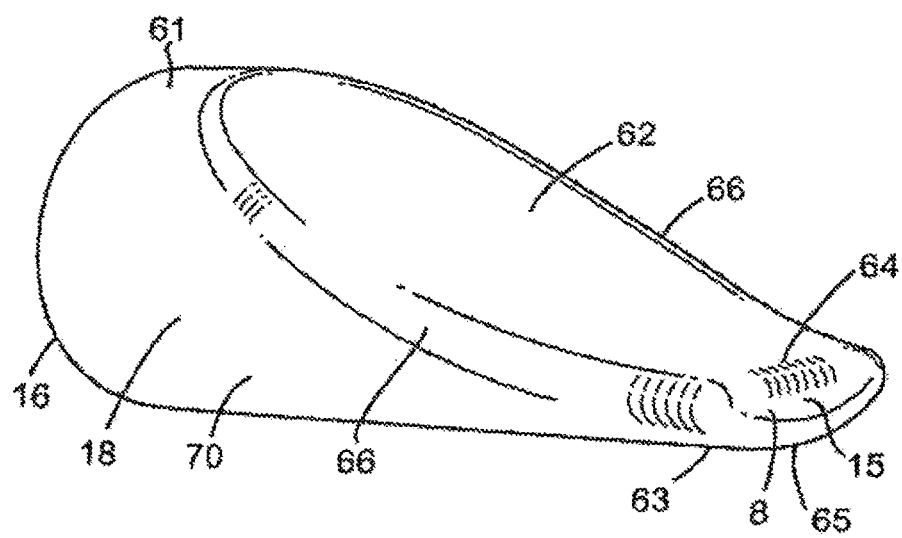
FIG. 14 is a perspective view of a portion of a guide wire according to a further embodiment of the invention.

Referring now to FIG. 14, there is illustrated a terminal member 70 of a guide wire (not shown) also according to the invention. In this embodiment of the invention the core wire and the sleeve of the guide wire are similar to the core wire 5 and the sleeve 10 of the guide wire 1 of FIGS. 1 to 10. The terminal member 70 is substantially similar to the terminal member 60 and similar components are identified by the same reference numerals. The main difference between the terminal member 70 and the terminal member 60 is that the first surface portion 62 is concave instead of convex. Otherwise, the terminal member 70 is similar to the terminal member 60. The advantage of providing the first surface portion 62 of concave shape as opposed to convex shape is that probing by the terminal member 70 may initially have less contact area due to the concave surface.

Figure 15:
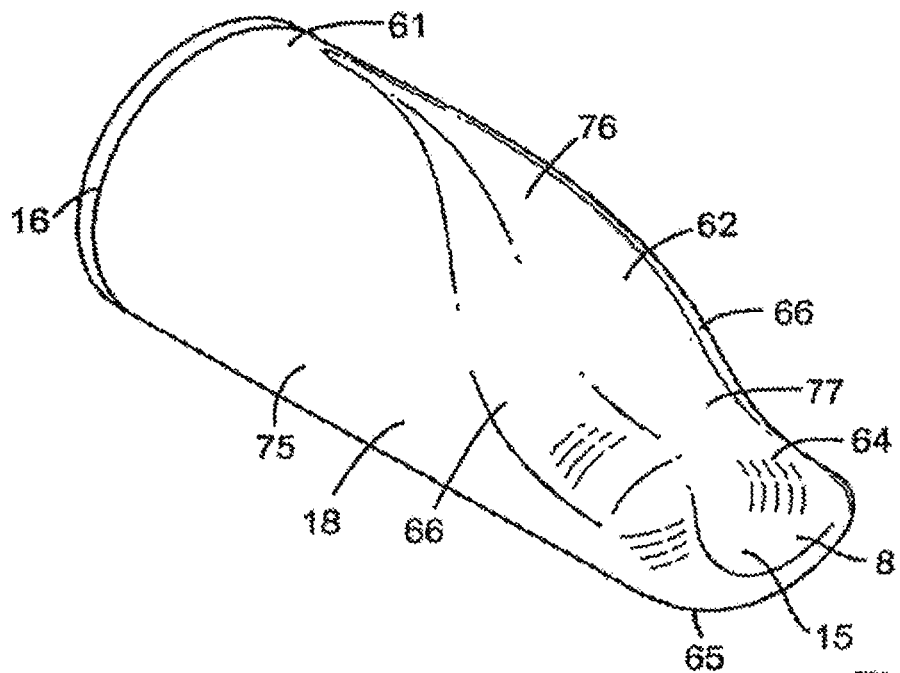
FIG. 15 is a perspective view of a portion of a guide wire according to a still further embodiment of the invention.

Referring now to FIG. 15, there is illustrated a terminal member 75 of a guide wire (not shown) also according to the invention. In this embodiment of the invention the core wire and the sleeve of the guide wire are similar to the core wire 5 and the sleeve 10 of the guide wire 1 of FIGS. 1 to 10. The terminal member 75 is substantially similar to the terminal member 60 and similar components are identified by the same reference numerals. The main difference between the terminal member 75 and the terminal member 60 is that the first surface portion 62 is formed sequentially by a proximal convex portion 76 and a distal concave portion 77. Additionally, the terminal member 75 is of a magnetic material, in this embodiment of the invention a ferrous material, so that the terminal member 75 can be urged through the vascular system, and also through an occlusion in a vessel of the vascular system by a magnetic field generated by a magnetic urging means (not shown), which would be located externally of the subject. Such an urging means, typically, would develop a magnetic field which could be moved and/or directed for urging the terminal member 75, and in turn, the guide wire (not shown) through the vascular system. Otherwise, the terminal member 75 is similar to the terminal member 60.

The advantage of providing the terminal member 75 of a magnetic material is that the member can be urged through the vascular system by an externally generated magnetic field, rather than, by urging the terminal member 75 through the vascular system by pushing the guide wire 1 into the subject. By virtue of the fact that the terminal member 75 is urged by a magnetic field through the vascular system, rather than by pushing the guide wire 1 into the subject, minimizes the danger of the terminal member 75 puncturing a vessel of the vascular system as the terminal member 75 is being urged therethrough. Additionally, by virtue of the fact that the guide wire is being pulled rather than being pushed, the guide wire can be provided with considerably more flexibility than could otherwise be provided if the guide wire were being pushed through the vascular system.

Referring now to FIGS. 16 to 18, there is illustrated a terminal member 80 of a guide wire also according to the invention, only a distal end portion 81 of the guide wire is illustrated. In this embodiment of the invention the core wire of the guide wire, the distal portion 28 of which is illustrated, and the sleeve 10, the distal portion also of which is illustrated, are similar to the core wire 5 and the sleeve 10 of the guide wire 1 of FIGS. 1 to 10. The terminal member 80 is also substantially similar to the terminal member 7 described with reference to FIGS. 1 to 10, and similar components are identified by the same reference numerals. In this embodiment of the invention the terminal member 80 is essentially formed by solder 82. The distal portion 28 of the core wire 5 extends beyond the sleeve 10, and is soldered to the sleeve 10 by the solder 82 which forms the terminal member 80. The leading edge portion 8 of the terminal member 80 is formed by a distal end 83 of the distal portion 28 of the core wire 5, and the solder 82 is shaped to form the first, second, third and fourth surface portions 13, 14, 18 and 21, respectively. However, in this embodiment of the invention the outer surface of the terminal member 80 at the proximal end portion 16 of the terminal member 80 formed by the solder 82 is of circular cross-section, and is of similar diameter to the outer diameter of the sleeve 10. Additionally, as well as the first and second surface portions 13 and 14 tapering towards the leading edge portion 8 of the terminal member 80, the third and fourth surface portions 18 and 21 also taper from the proximal end portion 16 of the terminal member 80 to the leading edge portion 8. The first, second, third and fourth surface portions 13, 14, 18 and 21, respectively, are radiused surfaces, and thus, are convex in transverse cross-section relative to the main central axis 6. The distal portion 28 of the guide wire 5 is centrally located in the sleeve 10, and accordingly, the plane containing the leading edge portion 8 also contains the main central axis 6 of the guide wire.

Otherwise, the guide wire and the terminal member 80 according to this embodiment of the invention is similar to the guide wire 1 and the terminal member 7, and their use is similar to that described with reference to the guide wire 1 of FIGS. 1 to 10.

Referring now to FIGS. 19 to 21, there is illustrated a terminal member 85 of a guide wire (not shown) also according to the invention. In this embodiment of the invention the core wire and the sleeve of the guide wire are similar to the core wire 5 and the sleeve 10 of the guide wire 1 of FIGS. 1 to 10. The terminal member 85 is substantially similar to the terminal member 7 of the guide wire 1 of FIGS. 1 to 10, and similar components are identified by the same reference numerals. The main difference between the terminal member 85 and the terminal member 7 is that in the terminal member 85 the leading edge portion 8 extends at an angle φ to the main central axis 6, which in this embodiment of the invention is approximately 70°.

Otherwise, the terminal member 85 and its use in conjunction with a guide wire is similar to the terminal member 7 of the guide wire 1 described with reference to FIGS. 1 to 10.

Referring now to FIGS. 22 and 23, there is illustrated a terminal member 90 of a guide wire (not shown) also according to the invention. In this embodiment of the invention the core wire and the sleeve of the guide wire are similar to the core wire 5 and the sleeve 10 of the guide wire 1 of FIGS. 1 to 10. The terminal member 90 is substantially similar to the terminal member 7 described with reference to FIGS. 1 to 10 and similar components are identified by the same reference numerals. The main difference between the terminal member 90 and the terminal member 7 is that firstly, the leading edge portion 8 extends at an angle φ to the main central axis 6, which in this embodiment of the invention is approximately 60.degree., and secondly, the third and fourth surface portions 18 and 21 converge from the proximal end portion 16 of the terminal member 90 to the leading edge portion 8. In this embodiment of the invention the first, second, third and fourth surface portions 13, 14, 18 and 21 are radiused, and thus are convex in a transverse direction relative to the main central axis 6.

Otherwise, the terminal member 90 is similar to the terminal member 7.

Referring now to FIGS. 24 and 25, there is illustrated a terminal member 95 of a guide wire (not shown) also according to the invention. In this embodiment of the invention the core wire and sleeve of the guide wire are similar to the core wire 5 and the sleeve 10 of the guide wire 1 of FIGS. 1 to 10. The terminal member 95 is substantially similar to the terminal member 7, and similar components are identified by the same reference numerals. The main difference between the terminal member 95 and the terminal member 7 is that the leading edge portion 8 is radiused in plan view, and thus, is convex in plan view. Otherwise, the terminal member 95 is similar to the terminal member 7.

Referring now to FIGS. 26 and 27, there is illustrated a terminal member 100 of a guide wire (not shown) also according to the invention. In this embodiment of the invention the core wire and the sleeve of the guide wire are similar to the core wire 5 to and the sleeve 10 of the guide wire 1 of FIGS. 1 to 10. The terminal member 100 is substantially similar to the terminal member 7, and similar components are identified by the same reference numerals. The main difference between the terminal member 100 and the terminal member 7 is that the leading edge portion 8 is radiused in plan view, and in this embodiment of the invention is concave in plan view. Otherwise, the terminal member 100 is similar to the terminal member 7.

Referring now to FIGS. 29 to 30, there is illustrated a terminal member 105 of a guide wire (not shown) also according to the invention. In this embodiment of the invention the core wire and the sleeve of the guide wire are similar to the core wire 5 and the sleeve 10 of the guide wire of FIGS. 1 to 10. The terminal member 105 is substantially similar to the terminal member 7, and similar components are identified by the same reference numerals. The main difference between the terminal member 105 and the terminal member 7 is that the portion of the terminal member which extends between the proximal end portion 16 and the leading edge portion 8 along which the first and second surface portions 13 and 14 taper towards the leading edge portion is twisted through an angle of approximately 90°. Otherwise, the terminal member 105 is similar to the terminal member 7, and the use of the terminal member 105 and its guide wire is similar to the guide wire 1 described with reference to FIGS. 1 to 10.

Figure 31:
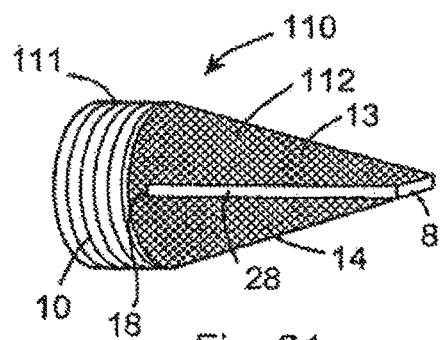
FIG. 31 is a perspective view of a portion of a guide wire according to another embodiment of the invention.
Figure 32:
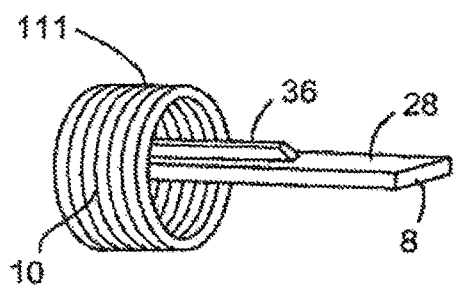
FIG. 32 is a perspective view of a part of the portion of the guide wire of FIG. 31.

Referring now to FIGS. 31 and 32, there is illustrated a terminal member 110 of a guide wire also according to the invention, only a distal portion 111 of the guide wire is illustrated in FIGS. 31 and 32. In this embodiment of the invention the core wire, the distal portion 28 of which is illustrated and the sleeve, a distal portion 10 of which is illustrated, of the guide wire are similar to the core wire 5 and the sleeve 10 of the guide wire 1 of FIGS. 1 to 10. The terminal member 110 is substantially similar to the terminal member 7 of the guide wire 1 of FIGS. 1 to 10, and similar components are identified by the same reference numerals. Additionally, the terminal member 110 of this embodiment of the invention is somewhat similar to the terminal member 80 described with reference to FIGS. 16 to 18. In this embodiment of the invention the terminal member 110 is essentially formed by solder 112 which solders the distal portion 28 of the guide wire to the sleeve 10 of the guide wire. The main difference between the terminal member 110 and the terminal member 80 is that in this embodiment of the invention the distal portion 28 of the core wire is wider than the distal portion of the guide wire of FIGS. 16 to 18, and thus, the leading edge portion 8 of the terminal member 110 is longer than the leading edge portion 8 of the terminal member 80. Additionally, the reinforcing rib 36 of the distal portion 28 of the core wire 5, in this embodiment of the invention, extends into the terminal member 110. The solder 112 is shaped to form the terminal member 110 in similar fashion as the solder 82 is shaped to form the terminal member 80.

Otherwise, the terminal member 110 is similar to the terminal member 80, which in turn is substantially similar to the terminal member 7.

Figure 33:
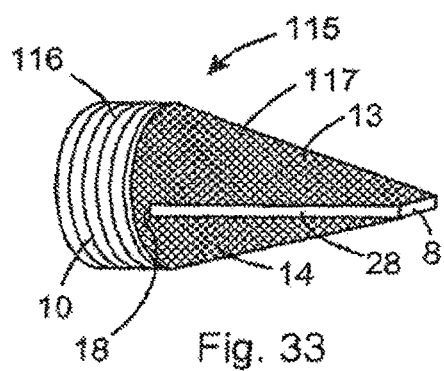
FIG. 33 is a perspective view of a portion of a guide wire according to another embodiment of the invention.
Figure 34:
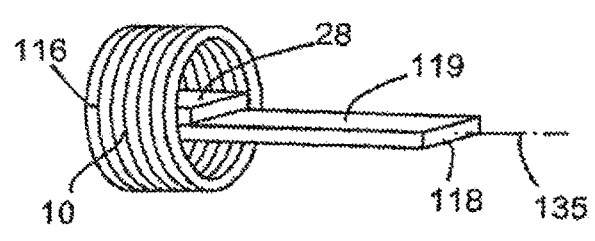
FIG. 34 is a perspective view of a part of the portion of the guide wire of FIG. 33.

Referring now to FIGS. 33 and 34, there is illustrated a terminal member 115 of a guide wire also according to the invention, only a distal end 116 of the guide wire is illustrated. In this embodiment of the invention the core wire and sleeve of the guide wire are similar to the core wire 5 and the sleeve 10 of the guide wire 1 of FIGS. 1 to 10. The terminal member 115 is substantially similar to the terminal member 110, which in turn is substantially similar to the terminal member 7, and similar components are identified by the same reference numerals. The main difference between the terminal member 115 and the terminal member 110 is that a distal portion extension 119 is secured to the distal portion 28 of the core wire 5, and is not centrally located in the sleeve 10. Rather, the distal portion extension 119 defines a central major plane 135, which is parallel to but offset from a plane containing the main central axis 6. As in the case of the terminal member 110, the terminal member 115 is essentially formed by solder 117, and accordingly, by virtue of the fact that the distal portion extension 119 is offset from the main central axis 6, the leading edge portion 8 of the terminal member 115, which is formed by a distal end 118 of the distal portion extension 119 of the core wire 5, is contained in a plane which extends parallel to a plane containing the main central axis 6 of the core wire, but is offset therefrom. Otherwise, the terminal member 115 is substantially similar to the terminal member 110, which in turn is substantially similar to the terminal member 7.

Figure 35:
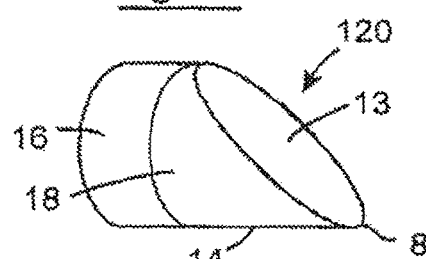
FIG. 35 is a perspective view of a portion of a guide wire according to a further embodiment of the invention.

Referring now to FIG. 35, there is illustrated a terminal member 120 of a guide wire (not shown) also according to the invention. In this embodiment of the invention the core wire and the sleeve of the guide wire are similar to the core wire 5 and sleeve 10 of the guide wire 1 of FIGS. 1 to 10. The terminal member 120 is substantially similar to the terminal member 7, and similar components are identified by the same reference numerals. The main difference between the terminal member 120 and the terminal member 7 is that in this embodiment of the invention only the first surface portion 13 is angled to converge with the second surface portion 14. Otherwise, the terminal member 120 is similar to the terminal member 7.

Figure 37:
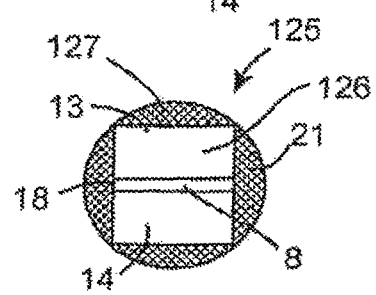
FIG. 37 is an end elevational view of the portion of the guide wire of FIG. 36.
Figure 36:
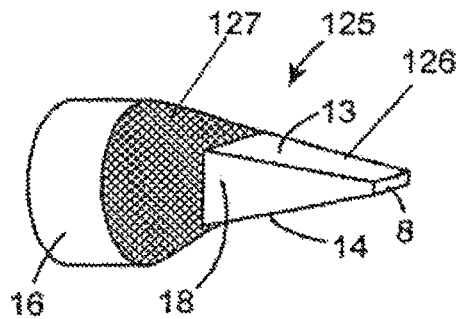
FIG. 36 is a perspective view of a portion of a guide wire according to a still further embodiment of the invention.

Referring now to FIGS. 36 and 37, there is illustrated a terminal member 125 of a guide wire (not shown) also according to the invention. In this embodiment of the invention the core wire and the sleeve of the guide wire are similar to the core wire 5 and the sleeve 10 of the guide wire 1 of FIGS. 1 to 10. The terminal member 125 is substantially similar to the terminal member 7, and similar components are identified by the same reference numerals. The main difference between the terminal member 125 and the terminal member 7 is that a leading portion 126 of the terminal member 125 is of wedge shape construction, and extends from an intermediate portion 127 which is located between the proximal end portion 16 and the leading portion 126. The leading portion 126 defines the leading edge portion 8 which extends transversely relative to the main central axis 6 of the guide wire, and is contained in a plane which also contains the main central axis 6.

The first and second surface portions 13 and 14 extend from the proximal end portion 16 to the leading edge portion 8 and converge along the intermediate portion 127 and the leading portion 126. However, the portion of the first and second surface portions 13 and 14, which are defined by the intermediate portion 127 are radiused, and thus, convex in a direction transversely of the main central axis 6, while the portion of the first and second surface portions 13 and 14 defined by the leading portion 126 are planar surfaces. The third and fourth surface portions 18 and 21, which are defined by the leading portion 126 are planar surfaces, and extend parallel to each other. However, the portions of the third and fourth surface portions 18 and 20 which are defined by the intermediate portion 127 converge from the proximal end portion 16 to the leading portion 126. The third and fourth surface portions 18 and 21 which are defined by the intermediate portion 127 are radiused, and thus, convex in a direction transversely of the main central axis 6 of the guide wire.

Otherwise, the terminal member 127 is similar to the terminal member 7.

Figure 38:
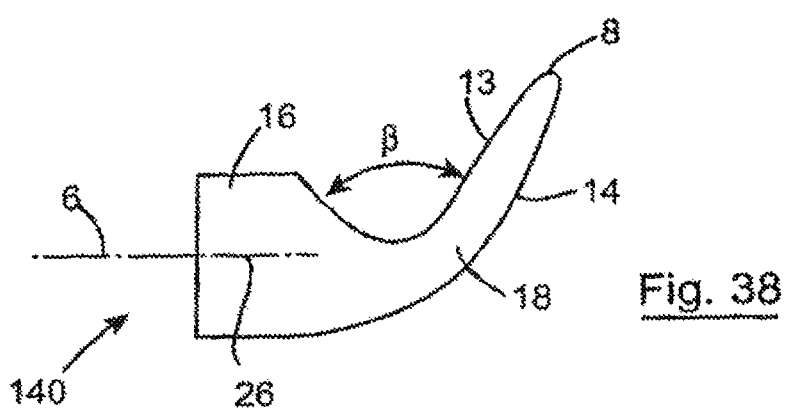
FIG. 38 is a side elevational view of a portion of a guide wire according to a still further embodiment of the invention.
Figure 39:
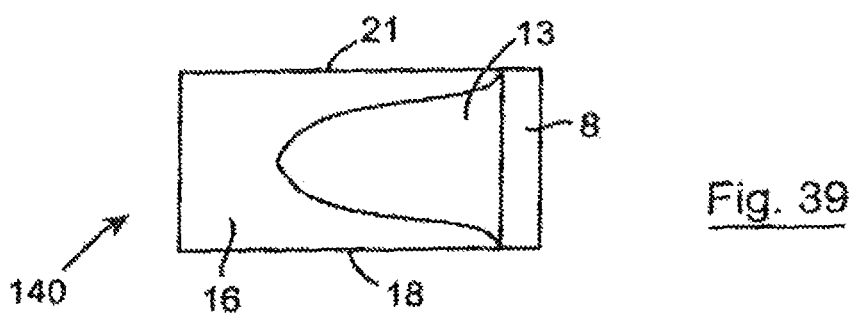
FIG. 39 is a top plan view of the portion of the guide wire of FIG. 38.

Referring now to FIGS. 38 and 39, there is illustrated a terminal member 140 of a guide wire (not shown) also according to the invention. In this embodiment of the invention the core wire and the sleeve of the guide wire are similar to the core wire 5 and the sleeve 10 of the guide wire 1 of FIGS. 1 to 10. The terminal member 140 is substantially similar to the terminal member 7, and similar components are identified by the same reference numerals. The main difference between the terminal member 140 and the terminal member 7 is that the acute angle $\alpha$ defined by the first and second surface portions 13 and 14 is less than the acute angle $\alpha$ defined by the first and second surface portions 13 and 14 of the terminal member 7, and accordingly, the length of the first and second surface portions 13 and 14 between the proximal end portion 16 and the leading edge portion 8 is longer in the terminal member 140 than it is in the terminal member 7. Additionally, the portion of the terminal member 140 extending between the proximal end portion 16 and the leading edge portion 8 is bent at an angle $\beta$ out of the central major plane 26 defined by the first and second surface portions 13 and 14, so that the leading edge portion 8 is offset from the main central axis 6, for facilitating guiding of the terminal member 140, and in turn the guide wire into a branching vessel. Otherwise, the terminal member 140 is similar to the terminal member 7, and its use along with the guide wire according to this embodiment of the invention is similar to that of the guide wire 1 described with reference to FIGS. 1 to 10.

While the guide wire according to the invention has been described for use in opening an occluded vessel in the cardiovascular system of a human or animal subject, it will be readily apparent to those skilled in the art that the guide wire according to the invention may be used for opening a vascular occlusion in any other vascular system of the human or animal body.

While the sleeve extending around the core wire 5 adjacent its distal end has been described as being provided by a helical coil, any other suitable sleeve may be provided, for example, in certain cases, it is envisaged that the sleeve may be provided as a sleeve of plastics material, composite polymer material, or any other polymer material.

It will be appreciated that the guide wire may be produced of materials other than those described, for example, the core wire may be of any other suitable material besides stainless steel, for example, nickel titanium alloy, MP35N; composite polymers, and the like. Similarly, the helical coil or other sleeve may be of any other suitable material besides stainless steel, for example, nickel titanium alloy, MP35N, composite polymers, and the like, and the terminal member may be of any other material besides platinum alloy, however, it is preferable that the terminal member or a portion thereof or a portion of the guide wire adjacent the terminal member should be of a radiopaque material. Where the terminal member is of a magnetic material, the magnetic material may be any other suitable magnetic material besides that described with reference to the terminal member 75 of FIG. 15. Indeed, in certain cases it is envisaged that the terminal member may be constructed only partly of a magnetic material. However, it is preferable that the terminal member, even where it is of a magnetic material, should be of a radiopaque material for facilitating tracking of the terminal member as it is being urged through the vascular system.

Needless to say, while only the terminal member 75 has been described as being of a magnetic material, it will be readily apparent to those skilled in the art that any of the other terminal members described may be of a magnetic material.

Needless to say, any other suitable securing means for securing the terminal member to the core wire and to the helical coil or other sleeve may be used besides soldering and brazing. Indeed, in certain cases, it is envisaged that the terminal member may be secured to the core wire and the helical coil or other sleeve by welding, adhesive or any other suitable securing means. It is also envisaged in certain cases that the terminal member may be integrally formed with the core wire from the same material.

Furthermore, while the terminal member in some of the embodiments of the invention described with reference to the drawings has been described as being formed or partly formed by solder, it will be appreciated that instead of the terminal member being formed or partly formed by solder, it may be formed or partly formed by any other suitable material, for example, a brazing material, a welding material, indeed, by an adhesive or any other suitable filler material.

It is also envisaged that while in some of the embodiments of the invention described with reference to the drawings the terminal member has been described as having a bore extending into the terminal member for engaging the distal portion of the core wire, in certain cases, it is envisaged that a plug portion may extend from the terminal member for securing to the distal portion of the core wire by any suitable securing means, for example, soldering, brazing, welding or adhesive. In which case, it is envisaged that, in general, the plug portion would be a relatively flat member in order to abut and lie parallel to one of the major surfaces of the distal portion of the core wire.

Additionally, while the terminal members of the guide wires described with reference to the drawings in general have been described as having first and second surface portions joined by third and fourth surface portions, which extend to the leading edge portion from the proximal end portion, it is envisaged in certain cases that a portion of the first surface portion may be formed by portions of the third and fourth surface portions, so that when viewed from the distal end of the terminal member in the direction of the proximal end thereof, the transverse cross-section of the terminal member would be substantially triangular. The base of the triangle forming the second surface portion and the leading edge portion, while the two sides of the triangle would form the third and fourth surface portions, or the first surface portion, depending on how the terminal member is viewed. In which case, it is envisaged that the surface portion of the terminal member forming the base of the triangle may be planar or convex when viewed in a transverse direction, and the portions of the surface of the terminal member forming the two sides of the triangle may be planar or convex when viewed in a transverse direction. In such cases, the first surface portion may be formed by the apex of the triangle defined by the third and fourth sides thereof, and the apex may be radiused or not radiused.

It is also envisaged that the third and fourth surface portions of the terminal member may be planar, convex or concave in a longitudinal direction, or may be a combination of one or more of planar, concave and convex in a longitudinal direction.

What is claimed is:

1. A guide wire, comprising:
    a) a core wire extending longitudinally along a main central axis to a proximal core wire end and a distal core wire portion having a distal core wire end, wherein the distal core wire portion comprises first and second major core wire surfaces joined by opposed third and fourth minor core wire surfaces, the first and second major core wire surfaces converging toward each other while the third and fourth minor core wire surfaces diverge away from each other;
    b) a terminal member connected to and extending axially from the distal core wire end, wherein the terminal member has opposed first and second planar terminal member surfaces that converge toward each other as they extend distally along the main central axis to a radiused leading edge, and wherein the first and second planar terminal member surfaces are joined by opposed third and fourth radiused terminal member surfaces, the third and fourth radiused terminal member surfaces being convex in a transverse direction relative to the central axis, wherein the radiused leading edge of the terminal member extends to and meets with the third and fourth radiused terminal member surfaces; and
    c) a reinforcing rib supported on one of the first and second major core wire surfaces, the reinforcing rib terminating proximal the distal core wire end.

2. The guide wire of claim 1 wherein an included angle between the first and second planar terminal member surfaces ranges from 5° to 6°.

3. The guide wire of claim 1 wherein an included angle between the first and second planar terminal member surfaces ranges from 12° to 30°.

4. The guide wire of claim 1 wherein a radius of the radiused leading edge of the terminal member ranges from 0.05 mm to 0.10 mm.

5. The guide wire of claim 1 wherein a proximal portion of the terminal member has an axially extending bore receiving the distal core wire end.

6. The guide wire of claim 5 wherein the distal core wire end is secured in the bore of the terminal member with a solder.

7. The guide wire of claim 1 wherein a helical coil sleeve is mounted on the core wire with the core wire extending through a bore of the helical coil sleeve.

8. The guide wire of claim 7 wherein a distal end of the coil sleeve is secured to a proximal end of the terminal member.

9. The guide wire of claim 8 wherein a first outer diameter of the distal end of the coil sleeve is similar to a second outer diameter of the proximal end of the terminal member.

10. The guide wire of claim 1 wherein the terminal member is of a radiopaque material.

11. The guide wire of claim 1 wherein the distal core wire portion comprising the converging first and second major core wire surfaces and the diverging third and fourth minor core wire surfaces provides the core wire comprising a spade-like configuration of a rectangular transverse cross-section.

12. The guide wire of claim 1 wherein the core wire is bendable so that a longitudinal axis of the terminal member is at an angle ranging from 90° to greater than zero with respect to main central axis of the core wire.

13. The guide wire of claim 1 wherein the terminal member is configured as being capable of being urged through an occlusion by a magnetic urging means.

14. A guide wire, comprising:
a) a core wire extending longitudinally along a main central axis to a proximal core wire end and a distal core wire portion having a distal core wire end, wherein the distal core wire portion comprises first and second major core wire surfaces joined by opposed third and fourth minor core wire surfaces, and wherein the first and second major core wire surfaces converge toward each other while the third and fourth minor core wire surfaces diverge away from each other;
b) a reinforcing rib supported on one of the first and second major core wire surfaces, the reinforcing rib terminating proximal the distal core wire end;
c) a terminal member connected to and extending axially from the distal core wire end, wherein the terminal member has opposed first and second planar terminal member surfaces that converge toward each other as they extend distally along the main central axis to a radiused leading edge, and wherein the first and second planar terminal member surfaces are joined by opposed third and fourth radiused terminal member surfaces, the third and fourth radiused terminal member surfaces being convex in a transverse direction relative to the central axis, wherein the radiused leading edge extends to and meets with the third and fourth radiused terminal member surfaces; and
d) a helical coil sleeve providing a bore receiving the distal core wire end with a distal end of the coil sleeve secured to a proximal end of the terminal member, wherein a first outer diameter of the distal end of the coil sleeve is similar to a second outer diameter of the proximal end of the terminal member.

15. The guide wire of claim 14 wherein the core wire is bendable so that a longitudinal axis of the terminal member is at an angle ranging from 90° to greater than zero with respect to the main central axis of the core wire.

16. A guide wire, comprising:
a) a core wire extending longitudinally along a main central axis to a proximal core wire end and a distal core wire portion having a distal core wire end, wherein the distal core wire portion comprises first and second major core wire surfaces joined by opposed third and fourth minor core wire surfaces, the first and second major core wire surfaces converging toward each other while the third and fourth minor core wire surfaces diverge away from each other;
b) a terminal member connected to and extending axially from the distal core wire end, wherein the terminal member has opposed first and second planar terminal member surfaces that converge toward each other as they extend distally along the main central axis to a radiused leading edge, and wherein the first and second planar terminal member surfaces are joined by opposed third and fourth radiused terminal member surfaces, the third and fourth radiused terminal member surfaces being convex in a transverse direction relative to the central axis, wherein the radiused leading edge extends to and meets with the third and fourth radiused terminal member surfaces; and
c) a helical coil sleeve providing a bore receiving the distal core wire end with a distal end of the coil sleeve secured to a proximal end of the terminal member,
d) wherein an included angle between the first and second planar terminal member surfaces ranges from 12° to 30° and a radius of the leading edge ranges from 0.05 mm to 0.10 mm.

\* \* \* \* \*